(12) United States Patent
Bouwens et al.

(10) Patent No.: US 6,596,895 B2
(45) Date of Patent: Jul. 22, 2003

(54) METHOD FOR THE CONTINUOUS PRODUCTION OF POLY CARBONATES

(75) Inventors: Stephan Mathys Bouwens, Bergen op Zoom (NL); Marcel Vieveen, Nieuw-Vossemeer (NL)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/683,833

(22) Filed: Feb. 21, 2002

(65) Prior Publication Data

US 2002/0107355 A1 Aug. 8, 2002

Related U.S. Application Data

(62) Division of application No. 09/713,692, filed on Nov. 15, 2000.

(51) Int. Cl.[7] .................................. C07C 69/96
(52) U.S. Cl. ................. 558/274; 558/270; 558/277
(58) Field of Search ................. 558/270, 274, 558/277

(56) References Cited

U.S. PATENT DOCUMENTS

| | | |
|---|---|---|
| 3,153,008 A | 10/1964 | Fox |
| 4,182,726 A | 1/1980 | Illuminati et al. |
| 4,552,949 A | 11/1985 | Mark |
| 4,554,110 A | 11/1985 | Mark .................. 260/463 |
| 4,680,374 A | 7/1987 | Hasuo et al. |
| 4,734,488 A | 3/1988 | Hasuo et al. |
| 4,745,029 A | 5/1988 | Kambour |
| 4,777,215 A | 10/1988 | Wehnert et al. |
| 4,902,746 A | 2/1990 | Serini et al. |
| 4,911,966 A | 3/1990 | Murayama et al. |
| 4,980,426 A | 12/1990 | Berg et al. |
| 5,025,081 A | 6/1991 | Fontana et al. |
| 5,132,154 A | 7/1992 | Westeppe et al. |
| 5,173,347 A | 12/1992 | Kanno et al. |
| 5,210,268 A | 5/1993 | Fukuoka et al. |
| 5,296,528 A | 3/1994 | Kütjens et al. |
| 5,334,742 A | 8/1994 | Schön et al. |
| 5,344,954 A | 9/1994 | Schön et al. |
| 5,380,908 A | 1/1995 | Murata et al. |
| 5,414,057 A | 5/1995 | Campbell et al. |
| 5,424,389 A | 6/1995 | Wimberger Friedl et al. |
| 5,455,323 A | 10/1995 | Fontana et al. |
| 5,459,229 A | 10/1995 | Kelsey et al. |
| 5,503,934 A | 4/1996 | Maas et al. |
| 5,567,802 A | 10/1996 | McCloskey |
| 5,605,980 A | 2/1997 | Boutni et al. |
| 5,646,233 A | 7/1997 | Sakashita et al. |
| 5,650,470 A | 7/1997 | McCloskey et al. |
| 5,670,605 A | 9/1997 | Sakashita et al. |
| 5,705,673 A | 1/1998 | Rivetti et al. |
| 5,783,653 A | 7/1998 | Okamoto |
| 5,859,172 A | 1/1999 | Sakashita et al. |
| 5,859,833 A | 1/1999 | Chatterjee et al. |
| 5,880,248 A | 3/1999 | Sakashita et al. |
| 5,883,194 A | 3/1999 | Saito et al. |
| 5,932,962 A | 8/1999 | Nakatani et al. |
| 6,093,842 A | 7/2000 | Oyevaar et al. ............ 558/274 |

FOREIGN PATENT DOCUMENTS

| | | |
|---|---|---|
| EP | 0 582 930 A2 | 8/1993 |
| EP | 0 842 685 | 5/1997 |

*Primary Examiner*—Sreeni Padmanabhan
*Assistant Examiner*—Ebenezer Sackey

(57) ABSTRACT

The present invention provides a method for making polycarbonates. One embodiment of the method comprises reacting diphenylcarbonate with a dihydric phenol. The diphenylcarbonate is made by reacting a reaction mixture comprising aryl alcohol together with a dialkyl carbonate in a reactor to produce aryl alkylcarbonate and diaryl carbonate.

20 Claims, 4 Drawing Sheets

FORMATION OF PHENYLMETHYLCARBONATE (PMC) FROM DMC AND PHENOL.

DISPROPORTIONATION OF PMC TO DPC AND DMC.

PRIOR ART

1= PHENOL & CATALYST PRE-HEATER
2= DMC PRE-HEATER
3= PLUNGER PUMPS
4= FEED UNIT FOR PHENOL/CATALYST
5= BOTTOM
6= REFLUX FEED POINT
8= SEPARATOR
9= DISCHARGE VALVE
10= PHENOL FEED VESSEL
11= DMC FEED VESSEL
12= TOWER 1
13= CATALYST FEED VESSEL

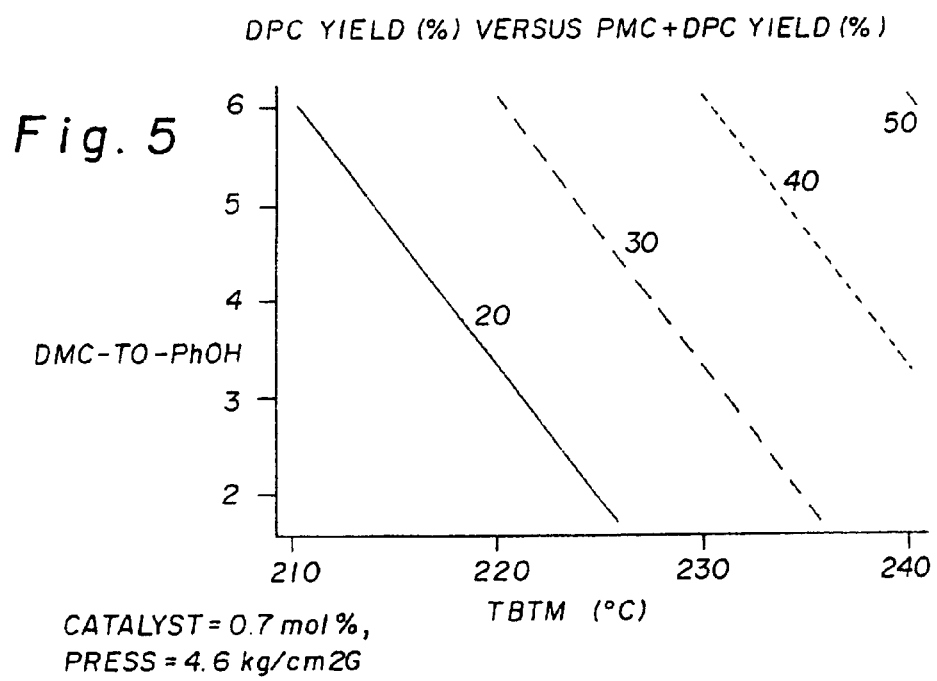
Fig. 5 DPC YIELD (%) VERSUS PMC+DPC YIELD (%)
CATALYST = 0.7 mol%, PRESS = 4.6 kg/cm2G
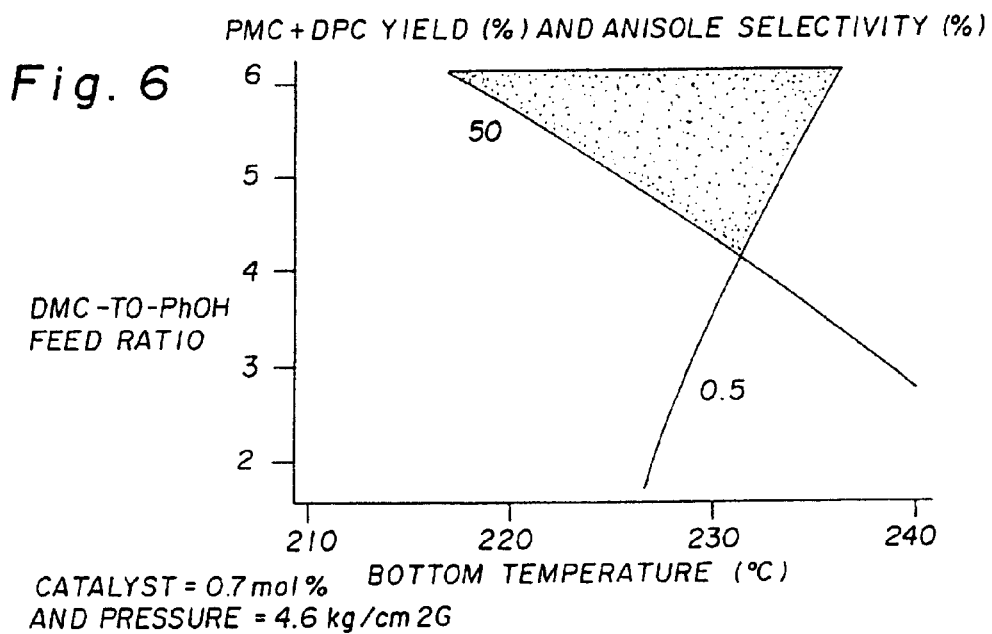
Fig. 6 PMC+DPC YIELD (%) AND ANISOLE SELECTIVITY (%)
CATALYST = 0.7 mol% AND PRESSURE = 4.6 kg/cm2G

METHOD FOR THE CONTINUOUS PRODUCTION OF POLY CARBONATES

CROSS REFERENCE TO RELATED APPLICATIONS

This application is a divisional application of U.S. patent application Ser. No. 09/713,692, filed Nov. 15, 2000, which is incorporated herein in its entirety.

BACKGROUND OF INVENTION

This application relates to the continuous production of aromatic carbonates by reaction of dialkyl carbonates and an aromatic alcohol in the presence of a catalyst.

Aromatic carbonates, such as diphenyl carbonate, are an important reactant in the production of polycarbonate resins. Polycarbonate resins are being used in an ever increasing number of applications. Therefore, the efficient production of diaryl carbonates has become more significant. Early processes for the production of diary carbonates used phosgene as a reagent. However, the toxicity of phosgene prompted the development of a non-phosgene process. As shown in FIG. 1, this non-phosgene process has two-steps. First, a dialkyl carbonate, such as dimethyl carbonate (DMC), reacts with an aromatic alcohol, such as phenol, to produce an alkyl aryl carbonate (e.g., phenyl methyl carbonate, PMC) and an alkyl alcohol (e.g., methanol). Next, two molecules of the alkyl aryl carbonate undergo a transesterification reaction to produce one molecule of diaryl carbonate (e.g., diphenyl carbonate, DPC) and one molecule of dialkyl carbonate (e.g., DMC).

Various methods and apparatus for making diaryl carbonates without using phosgene are known in the art. For example, U.S. Pat. No. 5,210,268, which is incorporated herein by reference, relates to a process for continuously producing aromatic carbonates. The process is carried out in a distillation column, wherein products are recovered from the bottom of the column, and low boiling by-products are removed from the top of the column. Other processes for production of diaryl carbonates using a series of distillation columns are disclosed in U.S. Pat. Nos. 5,344,954 and 5,705,673.

U.S. Pat. Nos. 5,705,673; 5,344,954; 5,334,742; 4,182,726, and 5,380,908 describe processes for making diaryl carbonates using apparatus which comprises at least two distillation columns: the first to produce phenyl methyl carbonate, and the second to convert the phenyl methyl carbonate into diphenyl carbonate. No commercially viable apparatus has been disclosed which is capable of producing sufficient yields of diphenyl carbonate in the first column to eliminate the necessity of a second column. A single column design would make the production process more economical. Accordingly, it would be most desirable to find a process wherein the yield of PMC and DPC versus the initial phenol feed is 50% or more, and the amount of DPC produced is maximized versus the total yield of PMC and DPC. Excess production of undesirable by-products such as phenyl methyl ether (i.e., anisole) should also be avoided.

It was discovered the above goals may all be accomplished by the present invention. Specifically, it is possible to obtain a 51% yield of PMC plus DPC with a selectivity to anisole byproduct of less than 0.2%, wherein the selectivity of DPC relative to the sum of PMC and DPC was 30 to 40%. The present invention therefore provides a method for continuous production of diphenyl carbonate which has a high production rate while at the same time providing an energy and raw material efficient process.

SUMMARY OF INVENTION

The present invention provides a method for making aromatic carbonates. In this method, an aryl alcohol is reacted with a dialkyl carbonate in a reactor (e.g., a distillation column) to produce a arylalkyl carbonate and diaryl carbonate. The total yield of arylalkyl carbonate and dialkyl carbonate together is at least 40%. Also, the selectivity of diaryl carbonate versus diaryl carbonate and arylalkyl carbonate together is preferably at least 25%.

In the method according to the present invention, the temperature measured at the bottom of the distillation column is preferably between 220 and 240° C., the DMC to phenol feed ratio is preferably between 4 and 7, the operating pressure measured at the top of the column is between 3 and 6 kg/cm$^2$ Gauge, and the amount of catalyst used is preferably from 0.5 to 1 molar percent.

In a more specific embodiment, the present invention provides a method for making aromatic carbonates in a distillation column having a lower reactive section and an upper rectification section. In this embodiment, a first reactive stream comprising an alcohol, and optionally a dialkyl carbonate and a catalyst, are fed into the top of the reactive section. A second stream containing a dialkyl carbonate, and optionally an aryl alcohol are fed into the bottom of the reactive section. The two streams are fed in sufficient quantities such that the weight ratio between the dialkyl carbonate and the aryl alcohol is from 4 to 6. The temperature measured at the bottom of the column is between 220° C. and 240° C., and the operating pressure measured at the top of the column is from 3 to 6 kg/cm$^2$ Gauge.

BRIEF DESCRIPTION OF DRAWINGS

FIG. 5 shows a graph depicting the relationship between DPC selectivity relative to total yield of PMC and DPC versus reaction temperature and DMC to phenol feed flow ratio.

FIG. 6 shows a graph depicting the relationship between PMC and DPC yield together with anisole selectivity as a function of reaction temperature and DMC to phenol feed flow ratio.

DETAILED DESCRIPTION

For purposes of the present application, the term "distillation column" shall refer to any sort of distillation column or reactive distillation column in which a process of distillation may be carried out.

For purposes of the present invention, the term "reaction mixture" includes the materials fed into the distillation column, which typically includes the aromatic alcohol and the dialkyl carbonate, and optimally a catalyst, arylalkyl carbonate, and other optional substances such as, for example entraining agents and/or solvents.

For purposes of the present application, the term "yield" or "total yield" shall refer to a weight percentage of the desired product(s) (e.g., aryl alkylcarbonates and diaryl carbonates) relative to the total weight of the mixture of products and reactant determined after obtaining a stable continuous operation.

For purposes of the present application, the term "selectivity" in the context of DPC shall refer to the weight ratio of DPC over the sum of the products DPC and PMC.

For purposes of the present application, the term "selectivity" in the context of anisole content shall refer to the weight ratio of anisole over the total weight of the mixture of products and reactants determined after obtaining a stable continuous operation.

For the purposes of the present application, the term "top of the column" is a relative term indicating a location within the upper 1/3 of a distillation column, which would include, but not necessarily be limited to, a position above the uppermost plate in said column.

For purposes of the present application, the term "bottom of the column" is a relative term indicating a location within the lower 1/3 of a distillation column, which would include, but not necessarily be limited to, a position below the lower most plate in said column.

For the purposes of the present application, the term "lower rectification section" shall refer to a lower section of a distillation column below the feeding point of at least one of the reactants wherein the chemical reaction is thought to occur in said section.

For purposes of the present application, the term "upper rectification section" shall refer to an upper section of a distillation column above the lower rectification section, wherein the chemical reaction is generally thought not to occur in said rectification section.

For the purposes of the present application, the term "operating pressure" is meant to refer to an average pressure reading during stable operation of the reaction, which pressure may vary throughout the process and upon start up and shut down.

For the purposes of the present application, technical terms not defined herein should be interpreted according to Grant & Hackh's Chemical Dictionary, 5$^{th}$ Ed., Roger Grant and Clair Grant, McGraw-Hill, Inc., 1987.

Relevant sections of all U.S. Patents referred to herein are all hereby incorporated by reference.

Figure 1:
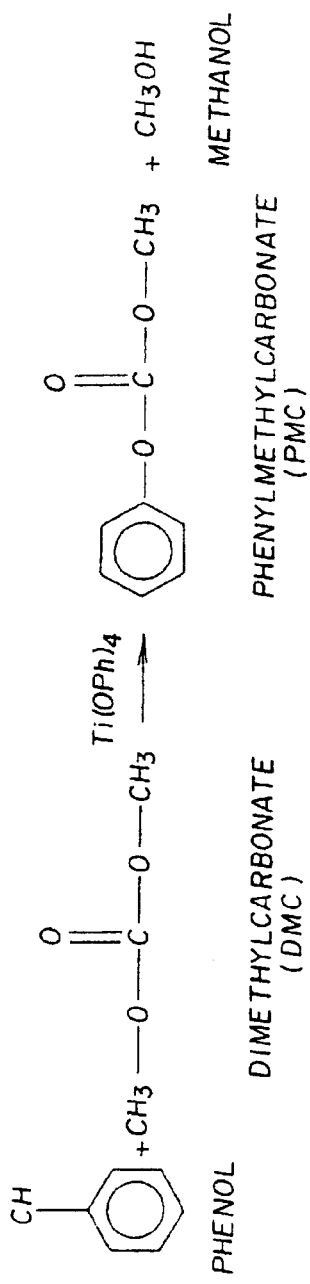
FIG. 1 shows the two-step reaction of dimethyl carbonate and phenol to produce diphenyl carbonate.
Figure 1:
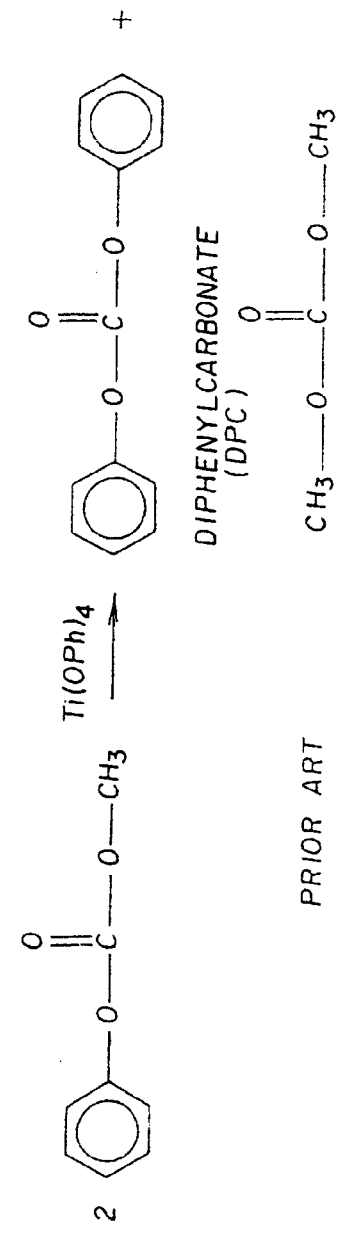

As shown in FIG. 1, the chemical reaction employed in the present invention is a reaction between an aromatic alcohol and a dialkyl carbonate. The aromatic alcohol and dialkyl carbonate should be selected such that they will undergo an exchange reaction with each other. FIG. 1 depicts a preferred reaction between phenol (an aromatic alcohol) and dimethyl carbonate (a dialkyl alcohol). FIG. 1 further depicts the disproportionation of one of the arylalkyl carbonate product, phenylmethylcarbonate, to form the diaryl carbonate product, diphenyl carbonate.

Suitable aromatic alcohols which are useful in the present reaction include phenol and alkylphenol such as cresol, xylenol, trimethyl-phenol, tetramethylphenol, ethylphenol, propylphenol, butylphenol, diethylphenol, methylethylphenol, methylpropylphenol, dipropylphenol, methylbutylphenol, pentylphenol, hexylphenol, cyclohexylphenol, and alkoxyphenols such as methoxyphenol and ethyoxyplenol. Suitable dialkyl carbonates which are useful in the present reaction include dimethylcarbonate, diethylcarbonate, methylethylcarbonate, ethylpropylcarbonate, dipropylcarbonate, propylbutylcarbonate, dibutylcarbonate, butylpentylcarbonate, dipentylcarbonate, pentylhexylcarbonate, dihexylcarbonate, hexylheptylcarbonate, diheptylcarbonate, heptyloctylcarbonate, dioctylcarbonate, octylnonylcarbonate, dinonylcarbonate, nonyldecylcarbonate, didecylcarbonate. It is also possible to use combinations of two or more aromatic alcohols and/or dialkyl carbonates.

The product diarylcarbonates are useful starting materials for preparing polycarbonates by reacting them with dihydric phenols (e.g., Bisphenol A) via the melt reaction. A very early description of the melt synthesis of polycarbonates is found in U.S. Pat. No. 3,153,008, but the patent literature is replete with further descriptions such as that found in U.S. Pat. No. 4,182,726.

Preferred classes of catalysts for conducting the reaction shown in FIG. 1 include titanium compounds like titaniumtetraphenoxide (Ti(OPh)$_4$), and Titaniumtetrachloride, organotin compounds, lead compounds, compounds of the copper family metals, zinc complexes, compounds of the iron family metals, and zirconium complexes. The catalyst selected should preferably have an activity of greater than 10 moles PMC/mole catalyst, but less than 400 moles PMC/mole catalyst. Typically, about 0.5 to 1.0 molar percent of the catalyst is used, and more preferably about 0.6 to 0.8 molar percent based on the phenol fed into the reaction. The catalyst is typically fed into one or more components of the reaction mixture before introduction into the distillation column, but it may be introduced into the column separately, before or during addition of the reaction mixture. The column may be kept under an inert atmosphere and may be pre-dried if desired.

As shown in the examples, the method according to the present invention is capable of producing very high yields. Under preferred conditions, the method may be used to produce a total yield of aryl alkyl carbonate plus diaryl carbonate of at least 40%, and optimally at least 50%. Also, the method is capable of producing total yields of diaryl carbonates versus total diaryl carbonates and arylakyl carbonates of greater than 25%, or more preferably 30%, or even 40%.

In order to achieve such high yields in a single column, the conditions within the distillation column must be carefully controlled. Specifically, the conditions for reacting DMC and phenol to make DMC and DPC should satisfy requirements (1) and (2) below:

(1) The catalyst should have a catalytic activity such that PMC is produced at a rate of 40 moles PMC per mole of catalyst wherein the reaction temperature is 210° C., the dialkyl carbonate is dimethyl carbonate, the aromatic hydroxy compound is phenol and the dimethyl carbonate/phenol ratio equals 3.2 (kg/kg) in the reaction system. In the case of Ti(OPh)$_4$, the optimum molar percent of catalyst is 0.7 based on the amount of phenol used. For systems using different reactants, optimum factors can be determined by repeating the experiments described in the Examples below, and by analyzing the data as shown herein.

Figure 3:
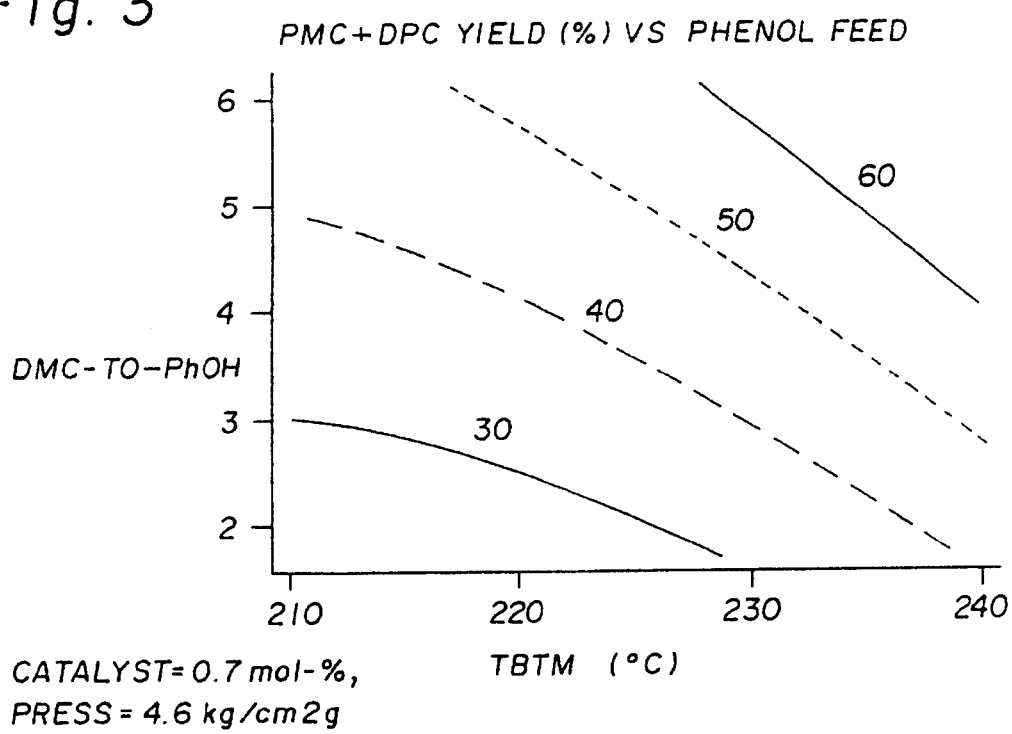
FIG. 3 shows a graph depicting the relationship between PMC and DPC yield versus reaction temperature and DMC to phenol feed flow ratio.

(2) The reaction should be conducted under conditions satisfying the following relational expressions:

$$a)\ PMC + DPC\ yield(\%) = -197.5 - 40.9*c + 4.07*r + 19.4*P - 0.930*T - 15.6*c^2 + 2.58*c*r - 0.294*c*T - 0.085*P*T$$

where c is the concentration of catalyst in molar percent based on hydroxy compound, r is the ratio of DMC flow rate (g/h) to phenol feed flow rate (g/h), P is the column pressure (in kg/cm$^2$ Gauge) and T is the reaction temperature (in ° C.). FIG. 3 shows this relation for different DMC to phenol flow ratios and reaction temperatures at constant catalyst amount (0.7 mol %) and constant pressure (4.6 kg/cm² Gauge). The target is a PMC+DPC yield greater or equal than 50%. As shown in FIG. 3, this target requires that reaction temperatures are higher than 220° C. and DMC to phenol feed flow ratios greater than 4 to 5.

b) Anisole selectivity(%) = $119.4 - 4.10*c + 2.59*r - 1.13*T +$
$$0.003*T^2 * 0.143*c*r +$$
$$0.023*c*T - 0.011*r*T$$

Figure 4:
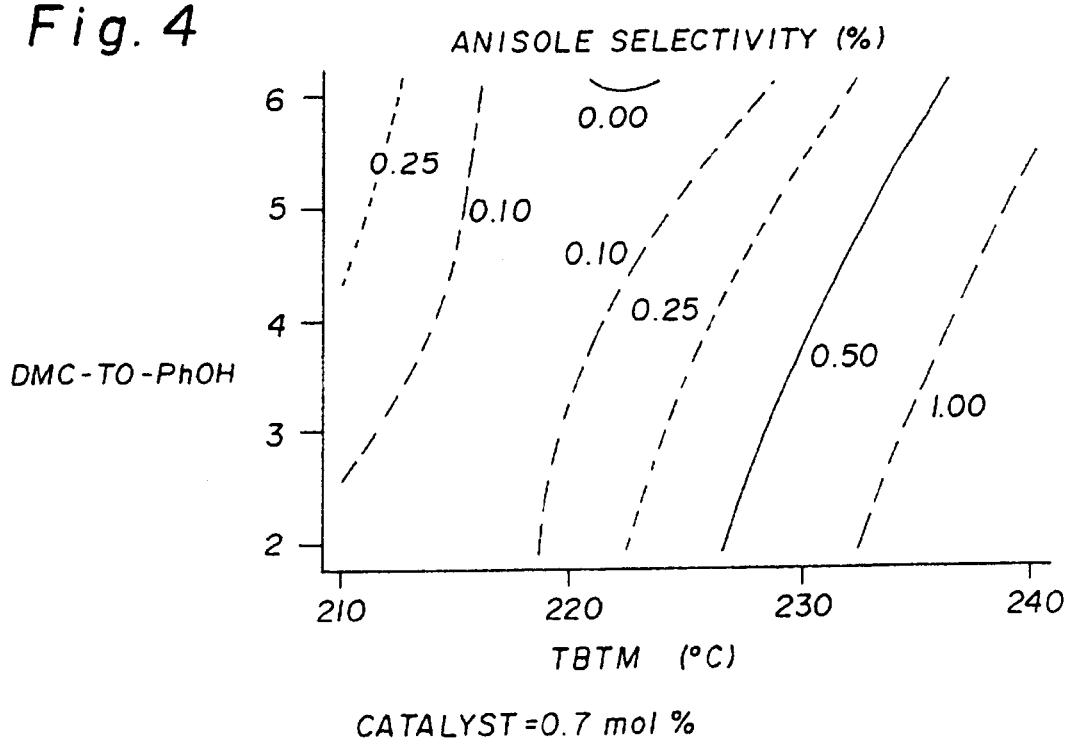
FIG. 4 shows a graph depicting the relationship between anisole selectivity versus reaction temperature and DMC to phenol feed flow ratio.

FIG. 4 shows this relation for different DMC to phenol flow ratios and reaction temperatures and at constant catalyst amount (0.7 mol %). The target anisole selectivity is less than or equal to 0.50%. As can be seen in FIG. 4, this target requires that reaction temperatures be less than 230 to 235° C., and that DMC to phenol feed flow ratios are higher than 4 to 5 (especially at high temperatures).

c) DPC selectivity versus PMC + DPC yield =
$$-237.5 - 84.9*c + 1.32*r + 19.5*P + 1.18*T -$$
$$12.98*c^2 + 3.37*c*r + 0.403*c*T - 0.098*P*T$$

FIG. 5 shows this relation for different DMC to phenol flow ratios and reaction temperatures at constant catalyst amount (0.7 mol %) and constant pressure (4.6 kg/cm² Gauge). The target is to maximize DPC yield versus PMC+DPC yield. It follows from FIG. 5 that maximum DPC yield versus PMC+DPC yield is obtained at high reaction temperatures and high DMC to phenol feed flow ratios.

Analysis of the above relational expressions reveals the following optimal operation conditions for the reaction of DMC and Phenol to form DPC and PMC:

The amount of catalyst (c): should be 0.5 to 1.0 molar percent, preferably 0.6 to 0.8 molar percent;

The column pressure (P): 3 to 6 kg/cm² Gauge, preferably 4 to 5 kg/cm² Gauge;

The reflux ratio should be between 0.2 and 3, preferably between 0.4 and 1.0;

The reaction temperature and DMC to phenol feed flow ratio are chosen according to the shaded region in FIG. 6. This region denotes the compilation of reaction temperatures and DMC to phenol feed flow ratios that result in a total yield of PMC and DPC of 50% or higher and in selectivity's to anisole of 0.5% or less. The shaded region of FIG. 6 was obtained after determining the overlap of total yield of PMC and DPC of 50% or more from FIG. 3, with anisole selectivity's of 0.5% or less from FIG. 4. It follows that the marked region consists of reaction temperatures between 220 and 235° C. and DMC to phenol feed flow ratios between 4 and 6. Remarkably, the marked region is also the region in which DPC selectivity relative to the total yield of PMC and DPC is high: between 30 and 45%, as shown in FIG. 5. Therefore, this region is a truly optimum region that meets the targets of maximizing yield and minimizing by-product formation. Without wishing to limit the invention to any single theory of operation, the reason for the high DPC yield versus PMC+DPC yield is thought to be the combination of high temperature and low to medium pressure. These two conditions result in low concentrations of DMC in the reactor mixture (DMC is a low boiling component) and high concentrations of PMC, so the disproportionation reaction of PMC to DPC and DMC is shifted towards the DPC side.

The present invention is further illustrated in a number of working examples, summarized in Table 1.

TABLE 1

|    | Feed streams |  |  |  | Reaction conditions |  |  |  | Results bottom product (*) |  |  |  | Performance (***) |  |  |
|----|---|---|---|---|---|---|---|---|---|---|---|---|---|---|---|
|    |  |  | DMC-to-Phenol (g/g) | Catalyst | Catalyst vs phenol (mole %) | Pressure (kg/cm² G) | Temp. at bottom (° C.) | Reflux ratio | Bottom flowrate (g/h) | PMC (wt %) | DPC (wt %) | Anisole (wt %) | PMC + DPC yield (%) | DPC yield/ PMC + DPC yield (%) | Anisole selectivity (%) |
| Nr | DMC (g/h) | Phenol (g/h) |  | (**) (g/h) |  |  |  |  |  |  |  |  |  |  |  |
| 1  | 1741 | 548 | 3.18 | 42.7 | 0.70 | 4.6 | 210 | 0.64 | 972 | 24.35 | 3.47 | 0.035 | 29.3 | 9.1 | 0.19 |
| 2  | 1739 | 549 | 3.17 | 42.7 | 0.70 | 4.6 | 210 | 0.64 | 971 | 24.26 | 3.49 | 0.022 | 29.3 | 9.5 | 0.12 |
| 3  | 1753 | 558 | 3.14 | 57.3 | 0.93 | 4.6 | 210 | 0.46 | 963 | 27.13 | 4.55 | 0.042 | 32.2 | 10.0 | 0.20 |
| 4  | 1820 | 546 | 3.33 | 39.3 | 0.65 | 4.6 | 210 | 0.69 | 948 | 26.73 | 4.26 | 0.028 | 32.2 | 11.0 | 0.16 |
| 5  | 1973 | 420 | 4.70 | 29.9 | 0.64 | 4.6 | 237 | 0.55 | 594 | 39.30 | 21.25 | 0.075 | 57.9 | 40.5 | 0.84 |
| 6  | 1890 | 403 | 4.69 | 26.9 | 0.60 | 4.6 | 237 | 0.57 | 565 | 40.04 | 22.19 | 0.039 | 59.1 | 41.2 | 0.99 |
| 7  | 1474 | 780 | 1.89 | 128.0 | 1.48 | 4.6 | 210 | 0.60 | 1483 | 18.09 | 1.81 | 0.032 | 17.8 | -19.2 | 0.35 |
| 8  | 1880 | 417 | 4.51 | 76.1 | 1.65 | 4.6 | 210 | 0.81 | 831 | 26.27 | 4.01 | 0.040 | 32.5 | 0.4 | 0.22 |
| 9  | 1880 | 417 | 4.51 | 76.1 | 1.65 | 4.6 | 240 | 0.32 | 682 | 40.11 | 22.62 | 0.152 | 66.1 | 38.6 | 0.41 |
| 10 | 1899 | 400 | 4.74 | 72.9 | 1.64 | 4.6 | 240 | 0.31 | 607 | 42.12 | 28.24 | 0.168 | 70.0 | 43.6 | 1.83 |
| 11 | 1478 | 777 | 1.90 | 128.0 | 1.49 | 4.6 | 240 | 1.07 | 1233 | 27.75 | 10.28 | 0.240 | 35.4 | 23.1 | 1.05 |
| 12 | 1485 | 787 | 1.89 | 11.1 | 0.13 | 4.6 | 210 | 1.24 | 1287 | 16.09 | 1.43 | 0.001 | 17.9 | 8.9 | 0.01 |
| 13 | 1516 | 784 | 1.93 | 10.8 | 0.12 | 4.6 | 232 | 0.44 | 1083 | 21.86 | 5.65 | 0.085 | 25.0 | 25.3 | 0.47 |
| 14 | 1940 | 390 | 4.97 | 5.7 | 0.13 | 4.6 | 210 | 0.33 | 692 | 22.73 | 2.84 | 0.041 | 29.0 | 14.0 | 0.26 |
| 15 | 1940 | 433 | 4.48 | 6.0 | 0.13 | 4.6 | 228 | 0.72 | 639 | 26.74 | 6.37 | 0.033 | 32.1 | 23.9 | 0.14 |
| 16 | 1955 | 438 | 4.46 | 6.1 | 0.13 | 4.6 | 210 | 0.33 | 733 | 23.72 | 3.01 | 0.051 | 28.4 | 13.5 | 0.27 |
| 17 | 1940 | 438 | 4.43 | 6.6 | 0.14 | 7.2 | 210 | 1.08 | 1043 | 19.08 | 1.25 | 0.043 | 30.1 | 6.7 | 0.36 |
| 18 | 1431 | 823 | 1.74 | 11.6 | 0.13 | 7.2 | 240 | 1.46 | 1282 | 22.84 | 3.85 | 0.232 | 26.8 | 17.8 | 1.39 |
| 19 | 1426 | 850 | 1.68 | 11.5 | 0.12 | 7.2 | 210 | 1.50 | 1885 | 12.25 | 0.50 | 0.001 | 17.3 | 2.7 | 0.01 |
| 20 | 1809 | 444 | 4.08 | 6.3 | 0.13 | 7.2 | 239 | 0.41 | 718 | 32.99 | 8.78 | 0.158 | 44.8 | 26.4 | 0.56 |
| 21 | 1808 | 420 | 4.31 | 76.1 | 1.64 | 7.2 | 210 | 0.49 | 1002 | 24.21 | 2.55 | 0.160 | 35.3 | -1.3 | 1.25 |
| 22 | 1401 | 768 | 1.82 | 143.0 | 1.68 | 7.2 | 240 | 0.62 | 1384 | 26.82 | 6.62 | 0.498 | 34.9 | 14.3 | 3.11 |
| 23 | 1418 | 801 | 1.77 | 131.4 | 1.48 | 7.2 | 210 | 2.53 | 1780 | 16.73 | 1.16 | 0.042 | 19.9 | -15.6 | 0.53 |

TABLE 1-continued

| | Feed streams | | | | Reaction conditions | | | Results bottom product (*) | | | | Performance (***) | | |
|---|---|---|---|---|---|---|---|---|---|---|---|---|---|---|
| Nr | DMC (g/h) | Phenol (g/h) | DMC-to-Phenol (g/g) | Catalyst (**) (g/h) | Catalyst vs phenol (mole %) | Pressure (kg/cm² G) | Temp. at bottom (° C.) | Reflux ratio | Bottom flowrate (g/h) | PMC (wt %) | DPC (wt %) | Anisole (wt %) | PMC + DPC yield (%) | PMC + DPC yield (%) | DPC yield/ PMC + DPC yield (%) | Anisole selectivity (%) |
| 24 | 1830 | 402 | 4.55 | 76.2 | 1.71 | 7.2 | 240 | 0.95 | 774 | 37.57 | 12.91 | 0.314 | 60.8 | 26.3 | 0.97 |
| 25 | 1885 | 309 | 6.09 | 22.7 | 0.66 | 4.6 | 231 | 0.47 | 474 | 41.03 | 22.21 | 0.067 | 66.1 | 41.2 | 0.09 |
| 26 | 1720 | 401 | 4.29 | 28.8 | 0.65 | 4.6 | 231 | 0.51 | 564 | 37.59 | 18.12 | 0.100 | 52.4 | 37.6 | 0.21 |
| 27 | 1876 | 356 | 5.27 | 26.1 | 0.66 | 4.6 | 227 | 0.47 | 530 | 38.18 | 14.76 | 0.049 | 52.2 | 32.6 | 0.10 |
| 28 | 1879 | 395 | 4.75 | 30.8 | 0.70 | 4.6 | 220 | 0.49 | 649 | 33.81 | 9.57 | 0.039 | 45.6 | 24.7 | 0.11 |
| 29 | 1884 | 369 | 5.10 | 20.9 | 0.51 | 4.6 | 227 | 0.47 | 539 | 37.91 | 15.15 | 0.056 | 51.2 | 33.1 | 0.11 |
| 30 | 1877 | 307 | 6.12 | 23.5 | 0.69 | 4.6 | 220 | 0.47 | 484 | 37.20 | 11.66 | 0.039 | 50.0 | 27.3 | 0.09 |
| 31 | 1889 | 365 | 5.18 | 25.2 | 0.62 | 4.6 | 226 | 0.46 | 534 | 37.57 | 14.50 | 0.063 | 50.2 | 32.3 | 0.13 |
| 32 | 2303 | 451 | 5.10 | 33.6 | 0.67 | 4.6 | 220 | 0.50 | 717 | 34.22 | 10.62 | 0.045 | 46.0 | 26.9 | 0.12 |

(*) Top product consists only of DMC (90–95 wt %) and methanol (5–10 wt %)
(**) Catalyst consists of 40.3 wt % of Titanium tetraphenolate, 36.5 wt % DPC and 23.2 wt % Heavies
(***) PMC yield = moles PMC generated per mole phenol in feed, DPC yield = moles DPC generated times 2 per mole phenol in feed, PMC + DPC yield = PMC yield plus DPC yield. Anisole selectivity = moles anisole generated per mole phenol converted

EXAMPLE 1

Figure 2:
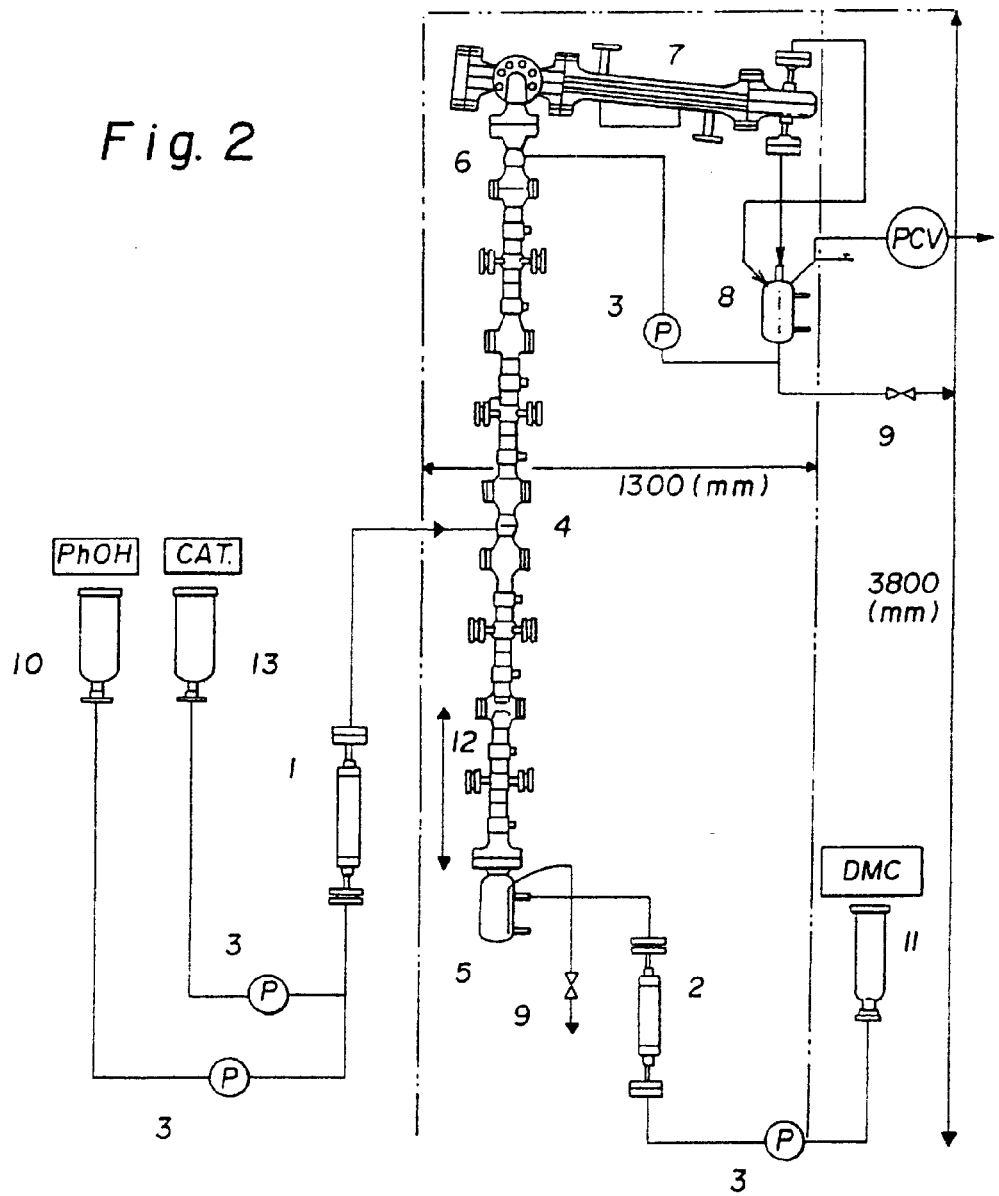
FIG. 2 shows schematic diagram of an apparatus in accordance with the invention.

A pilot distillation column (stainless steel) as shown in FIG. 2 was equipped with 40 perforated plates. The plate diameters were 50 mm for the bottom 20 trays and 40 mm for the top 20 trays. The total height of the column was 3.4 m, with a plate-to-plate distance of 50 mm for the bottom 20 trays and 40 mm for the top 20 trays. The holdup of the bottom 20 trays was 471 ml of liquid, the holdup of the bottom compartment of the column was 460 ml. Heat was supplied at the bottom of the column and to the bottom 20 trays of the column by means of electric heating mantles. The phenol feed (548 g/h) and catalyst feed (Titanium tetraphenolate (40.3 wt-%) dissolved in a mixture of DPC (36.5 wt-%) and heavies (23.2 wt-%), flow rate is 42.7 g/h) were mixed (resulting in a catalyst percentage of 0.70 mole-% versus phenol), preheated to 145° C. and then fed to tray 20 of the column. DMC (1741 g/h) was preheated to 145° C. and fed to the bottom compartment of the column below the first tray. The column was operated at a temperature of 210° C. at the bottom of the column, at a pressure of 4.6 kg/cm² Gauge measured at the top of the column, and with a reflux ratio of 0.64. The overhead was cooled to 90° C. in a condenser and part of the overhead was sent back as reflux to the top of the column. To compensate for heat losses to the environment, the bottom 20 trays were heated such that tray 7 (counting from the bottom tray) was kept at 5° C. below the bottom temperature and tray 12 (counting from the bottom tray) was kept at 10° C. below the bottom temperature. Table 1 shows the bottom flow rate and bottom flow composition under steady state conditions. Table 1 also includes the PMC+DPC yield, the DPC yield relative to the PMC+DPC yield and the selectivity for anisole. The top stream always consisted of DMC and methanol and is not included in the Table 1.

EXAMPLES 2 TO 32

Using the same apparatus described in Example 1, experiments were carried out under the reaction conditions indicated in Table 1. Results are shown in Table 1. examples 25 TO 32 correspond to preferred conditions according to the present invention.

EXAMPLE 33

The results shown in Table 1 were analyzed and fitted into a model using a "Custom Response Surface Design" from the software package Minitab® for Windows, Release 12.2. The commercially available software operates by using a response surface method to determine the relationship between one or more response variables (for instance Yield or Selectivity) and a set of quantitative experimental variables or factors (for instance Temperature, Pressure, reactant concentrations, etc.). The experimental data are fitted into a model. The type of model is chosen by the user. For instance, the user can choose a linear or a quadratic model. The fitting itself is done via a Least Squares method. The computational method is Givens transformations using Linpack routines. The method is described in: Linpack (1979), Linpack User's Guide by J. J. Dongarra, J. R. Bunch, C. B. Moler, and G. W. Stewart, Society for Industrial and Applied Mathematics, Philadelphia, Pa., which is incorporated by reference herein. Other known curve fitting methods could also be used.

Although the present invention has been described in considerable detail with reference to certain preferred versions thereof, other versions are possible. For example, the reaction could be conducted in a type of reactor other than a distillation column. Alternatively, the reaction could be conducted in a reaction column connected to a distillation column. Also, the reaction could be conducted using a fixed catalyst bed rather than using a homogeneous catalysts. Also, many other variations are possible. Therefore, the spirit and scope of the appended claims should not be limited to the description of the preferred versions contained herein.

What is claimed is:

1. A continuous method for making polycarbonates in a single distillation column which comprises reacting diphenylcarbonate with a dihydric phenol, wherein the diphenylcarbonate is made by reacting a reaction mixture comprising aryl alcohol together with a dialkyl carbonate to produce aryl alkylcarbonace and diaryl carbonate wherein the total yield of arylalkyl carbonate and diaryl carbonate together is at least 40%.

2. A continuous method for making polycarbonates in a single distillation column which comprises reacting diphenylcarbonate with a dihydric phenol, wherein the diphenylcarbonate is made by reacting a reaction mixture comprising aryl alcohol together with a dialkyl carbonate to produce aryl alkylcarbonate and diaryl carbonate wherein the total yield of arylalkyl carbonate and diaryl carbonate together is at least 25%.

3. The method according to claim 2, wherein the reaction mixture consists essentially of an aryl alcohol and dialkyl carbonate.

4. The method according to claim 2, wherein the reaction mixture consists essentially of an aryl alcohol, a dialkyl carbonate, and a catalyst.

5. The method according to claim 2, wherein the reaction mixture consists of an aryl alcohol and a dialkyl carbonate.

6. The method according to claim 2, wherein the reaction mixture consists of an aryl alcohol, a dialkyl carbonate, and a catalyst.

7. The method according to claim 2, wherein the aryl alcohol is phenol and dialkyl carbonate is dimethyl carbonate.

8. The method according to claim 7, further comprising an anisole with a selectivity less than 0.5% of moles phenol converted.

9. The method according to claim 7, wherein a weight ratio of dialkyl carbonate to aryl alcohol is from 4 to 6.

10. The method according to claim 7, wherein a temperature measured at the bottom of the column is between 220° C. and 240° C., a temperature measured at the top of the column is between 110° C. and 210° C. and an operating pressure measured at the top of the column is from 3 kg/cm² Gauge.

11. The method according to claim 7, wherein a column reflux ratio is between 0.2 and 3.

12. The method of claim 7, wherein a column reflux ratio is between 0.2 and 3, and an operating pressure measured at the top of the column is from 3 Kg/cm² Gauge to 6 Kg/cm² Gauge.

13. A continuous method for making polycarbonates in a single distillation column which comprises reacting diphenylcarbonate with a dihydric phenol, wherein the diphenylcarbonate is made by feeding a first stream comprising an aryl alcohol and a catalyst to a top subsection of a reactive section of the single distillation column comprising a lower reactive section having the top subsection, a bottom subsection, and an upper rectification section; feeding to the bottom subsection of the reactive section a second stream containing a dialkylcarbonate, wherein the first and second streams are fed in sufficient quantities such that the weight ratio between the dialkyl carbonate and aryl alcohol fed into the single distillation column is between 4 and 6, and a temperature at the bottom of the column is between 220° C. and 240° C., wherein an operating pressure of the column measured at the top of the column is from 3 to 6 kg/cm² Gauge, and wherein the reaction is carried out in the presence of a catalyst based on alkoxides or aryl oxides of titanium, wherein said catalyst is present in a quantity of from 0.5 to 1.0 molar percent based on the aryl alcohol.

14. The method according to claim 13, wherein a column reflux ratio is between 0.2 and 3.

15. The method according to claim 13, wherein the lower reactive section comprises at least 3 theoretical distillation steps, and the upper rectification section comprises at least 3 theoretical distillation steps.

16. The method according to claim 13, wherein, a temperature measured at the top of the column is between 110° C. and 210° C.

17. The method according to claim 13, wherein the aryl alcohol is phenol and the dialkylcarbonate is dimethyl carbonate.

18. The method according to claim 17, wherein the weight ratio between dimethylcarbonate and aryl alcohol fed into the distillation column is from 4.5 to 6.

19. The method according to claim 18, wherein the temperature at the bottom of the column is from 225° C. to 235° C.

20. The method according to claim 19, wherein the catalyst is titanium tetraphenolate.

* * * * *